United States Patent [19]

Johnson et al.

[11] Patent Number: 5,475,020
[45] Date of Patent: Dec. 12, 1995

[54] INDOLYL COMPOUNDS AND THEIR USE IN TREATMENT OF CEPHALIC PAIN

[75] Inventors: Martin R. Johnson; Peter C. North, both of Ware, England

[73] Assignee: Glaxo Group Limited, London, England

[21] Appl. No.: 256,089

[22] PCT Filed: Jan. 12, 1993

[86] PCT No.: PCT/EP93/00074
§ 371 Date: Jun. 27, 1994
§ 102(e) Date: Jun. 27, 1994

[87] PCT Pub. No.: WO93/14087
PCT Pub. Date: Jul. 22, 1993

[30] Foreign Application Priority Data

Jan. 16, 1992 [GB] United Kingdom ............... 9201038

[51] Int. Cl.[6] .................... A61K 31/405; C07D 403/04
[52] U.S. Cl. ............................... 514/414; 548/466
[58] Field of Search .................. 548/466; 514/414

[56] References Cited

U.S. PATENT DOCUMENTS 3,506,683  4/1970  Anthony et al. ..................... 548/466

FOREIGN PATENT DOCUMENTS

| | | | |
|---|---|---|---|
| 263476 | 5/1964 | Australia ............................ | 548/466 |
| 0254433 | 1/1988 | European Pat. Off. ...... | C07D 209/16 |
| 0450345 | 10/1991 | European Pat. Off. ...... | C07D 453/02 |
| 0497512 | 8/1992 | European Pat. Off. ...... | C07D 403/06 |
| 3700407 | 7/1987 | Germany ..................... | C07D 209/14 |
| 893899 | 4/1962 | United Kingdom ............... | 548/466 |
| WO-A9118897 | 12/1991 | WIPO ......................... | C07D 413/06 |

*Primary Examiner*—Jacqueline Haley
*Attorney, Agent, or Firm*—Bacon & Thomas

[57] ABSTRACT

The invention relates to indoles of general formula (I)

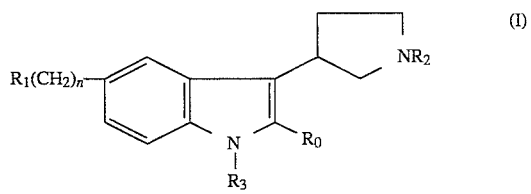

wherein $R_0$ represents a hydrogen atom or a $C_{1-3}$ alkyl group; $R_1$ represents a group $R_4CONH-$, $R_4R_5NSO_2-$, $R_4SO_2NH-$ or $R_4R_5NCO-$ (where $R_4$ is a hydrogen atom or a $C_{1-6}$ alkyl group, provided that $R_4$ does not represent a hydrogen atom when $R_1$ represents $R_4SO_2NH-$, and $R_5$ is a hydrogen atom or a $C_{1-6}$ alkyl, $C_{3-7}$cycloalkyl, phenyl or phen($C_{1-3}$)alkyl group in which the phenyl ring is optionally substituted by a halogen atom or a $C_{1-4}$ alkoxy, hydroxy or $C_{1-3}$alkyl group); $R_2$ is a hydrogen atom, a $C_{1-3}$alkyl, a $C_{3-6}$alkenyl, a phenyl or a phen($C_{1-3}$)alkyl group; $R_3$ is a hydrogen atom, a $C_{1-3}$alkyl group or a group $-CO_2R_6$, $-COR_6$, $-COCO_2R_6$ or $-CONHR_6$ where $R_6$ is a hydrogen atom or a $C_{1-4}$alkyl, a $C_{3-7}$ cycloalkyl, a $C_{3-6}$ alkenyl, an aryl or an ar($C_{1-4}$)alkyl group in which the aryl group may be unsubstituted or substituted by a halogen atom or a $C_{1-4}$ alkoxy, $C_{1-4}$ alkyl or hydroxy group, provided that when $R_3$ is $-CO_2R_6$, $R_6$ is other than hydrogen; n is zero or an integer from 1 to 5; and pharmaceutically acceptable salts thereof.

21 Claims, No Drawings

INDOLYL COMPOUNDS AND THEIR USE IN TREATMENT OF CEPHALIC PAIN

This application is a National Stage of PCT/EP93/00074, filed Jan. 12, 1993 and now WO93/10487, published Jul. 22, 1993.

This invention relates to indole derivatives, to processes for their preparation, to pharmaceutical compositions containing them and to their medical use, in particular to compounds and compositions of use in the treatment of migraine.

It has been suggested that the pain of migraine may be associated with excessive dilatation of the cranial vasculature and known treatments for migraine include the administration of compounds having vasoconstrictor properties such as ergotamine. However, ergotamine is a non-selective vasoconstrictor which constricts blood vessels throughout the body and has undesirable and potentially dangerous side effects. Migraine may also be treated by administering an analgesic usually in combination with an antiemetic but such treatments are of limited value.

More recently, indole derivatives which are selective $5HT_1$-like receptor agonists and which exhibit selective vasoconstrictor activity have been described in the art as useful in the treatment of migraine.

We have now found a novel group of indole derivatives which exhibit $5HT_1$-like receptor agaonist activity and selective vasoconstriction.

Thus, the present invention provides a compound of formula (I):

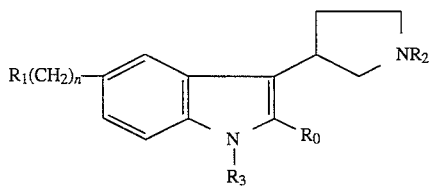

wherein $R_0$ represents a hydrogen atom or a $C_{1-3}$ alkyl group;

$R_1$ represents a group $R_4CONH-$, $R_4R_5NSO_2-$, $R_4SO_2NH-$ or $R_4R_5NCO-$ (where $R_4$ represents a hydrogen atom or a $C_{1-6}$ alkyl group, provided that $R_4$ does not represent a hydrogen atom when $R_1$ represents $R_4SO_2NH-$, and $R_5$ represents a hydrogen atom or a $C_{1-6}$ alkyl, $C_{3-7}$ cycloalkyl, phenyl or phen ($C_{1-3}$)alkyl group in which the phenyl ring is optionally substituted by a halogen atom or a $C_{1-4}$ alkoxy, hydroxy or $C_{1-3}$ alkyl group); $R_2$ represents a hydrogen atom or a $C_{-3}$ alkyl, $C_{3-6}$ alkenyl, phenyl or phen($C_{1-3}$)alkyl group; $R_3$ represents a hydrogen atom, a $C_{1-3}$ alkyl group or a group $-CO_2R_6$, $-COR_6$, $-COCO_2R_6$ or $-CONHR_6$ where $R_6$ represents a hydrogen atom or a $C_{1-4}$ alkyl, $C_{3-7}$ cycloalkyl, $C_{3-6}$ alkenyl, aryl or ar($C_{1-4}$)alkyl group in which the aryl group may be unsubstituted or substituted by a halogen atom or a $C_{1-4}$alkoxy, $C_{1-4}$alkyl or hydroxy group (provided that when $R_3$ represents $-CO_2R_6$, $R_6$ is other than hydrogen);

n represents zero or an integer from 1 to 5;

and pharmaceutically acceptable salts thereof.

As used herein an alkyl group either as such or as part of a phenalkyl, alkoxy or alkoxycarbonyl group may be a straight chain or branched chain alkyl group, for example a methyl, ethyl, or prop-2-yl group. A $C_{1-6}$ alkyl group is conveniently $C_{1-3}$ alkyl such as methyl. A $C_{3-7}$ cycloalkyl group may be a cyclopropyl, cyclobutyl, cyclopentyl, cyclohexyl or cycloheptyl group.

When $R_5$ represents a substituted or unsubstituted phen ($C_{1-3}$)alkyl group, the alkyl moiety of the group is preferably methyl.

A halogen substitutent may be a fluorine, chlorine, bromine or iodine atom. A $C_{1-4}$ alkoxy group may be, for example, a methoxy or ethoxy group.

An aryl group, either as such or as part of an ar($C_{1-4}$)alkyl group is preferably phenyl. Where $R_2$ and/or $R_6$ represents an alkenyl group it will be understood that no double bond may be adjacent to the nitrogen atom. An alkenyl group may for example be a 2-propenyl or butenyl group.

In one preferred class of compounds of formula (I), $R_1$ represents a group $R_4CONH-$.

In another preferred class of compounds of formula (I), $R_1$ represents a group $R_4R_5NSO_2-$, for example $CH_3NHSO_2-$.

Another preferred class of compounds of formula (I) is that in which $R_1$ represents a group $R_4SO_2NH-$.

In a further preferred class of compounds of formula (I), $R_1$ represents a group $R_4R_5NCO-$, for example $H_2NCO-$.

In the compounds of formula (I) $R_2$ preferably represents a $C_{1-3}$ alkyl group such as methyl or a hydrogen atom.

In one preferred class of compounds of formula (I) $R_3$ preferably represents a hydrogen atom.

The substituent $R_4$ may be, for example, a $C_{1-3}$ alkyl group such as methyl or a hydrogen atom.

$R_5$ in the compounds of formula (I) preferably represents a $C_{1-3}$ alkyl group such as methyl.

Conveniently $R_4$ and $R_5$ when considered together comprise from 1 to 3 carbon atoms.

In an alternative preferred class of compounds of formula (I), $R_4$ and $R_5$ both represent hydrogen atoms.

In one preferred class of compounds of formula (I), n represents zero or an integer from 1 to 3.

An alternative preferred class of compounds within the scope of formula (I) has the formula (Ia)

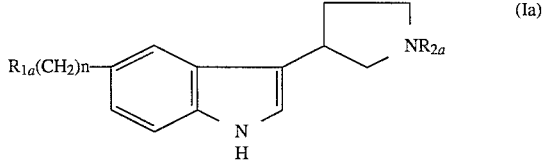

wherein $R_1a$ represents a group $R_{3a}R_{4a} NSO_2-$ (where $R_{3a}$ and $R_{4a}$ are the same or different and are hydrogen or a $C_{1-6}$ alkyl, preferably $C_{1-3}$ alkyl group such as methyl;

$R_2a$ represents a $C_{1-3}$ alkyl group (such as methyl) or a hydrogen atom;

n is an integer 1 or 2;

and pharmaceutically acceptable salts thereof.

Preferred compounds according to the invention include: N-methyl-3-(1-methyl-3-pyrrolidinyl)-1H-indole-5-ethanesulphonamide; N-Methyl-3-(1-methyl-3-pyrrolidinyl)-1H-indole-5-methanesulphonamide; and pharmaceutically acceptable salts thereof.

Suitable pharmaceutically acceptable salts are those conventionally known in the art. Examples of pharmceutically acceptable salts include acid addition salts formed with inorganic acids, such as hydrochlorides, hydrobromides, phosphates and sulphates, and with organic acids, for example tartrates, maleates fumarates, succinates and sulphonates. Other salts which are not pharmaceutically acceptable may be useful in the preparation of compounds of formula (I) and these form a further part of the invention.

It will be appreciated that the carbon atom attached to the 3-position of the indole nucleus is asymmetric and may exist in the R- or S-configuration. The present invention embraces both the individual forms of the compounds of formula (I) and all mixtures including racemic mixtures thereof. The invention also includes within its scope all geometric isomers of the compounds of formula (I).

Compounds of the invention may readily be isolated in association with solvent molecules by crystallisation from or evaporation of an appropriate solvent. It is intended to include such solvates within the scope of the present invention.

The slective $5HT_1$-like recptor agonist activity and selective vasoconstrictor activity of the compounds of the invention have been demonstrated in vitro. In addition, compounds of the invention selectively constrict the carotid arterial bed of the anaesthetised dog whilst having negligible effect on blood pressure.

Compounds of the invention are useful in treating conditions associated with cephalic pain such as cluster headache, chronic paroxysmal hemicrania, headache associated with vascular disorders, headache associated with substances or their withdrawal (for example drug withdrawal), tension headache and in particular migraine, and in alleviating the symptoms associated therewith.

Accordingly, the invention also provides a pharmaceutical composition which comprises at least one compound of formula (I) or a pharmaceutically acceptable salt or solvate (e.g. hydrate) thereof and formulated for administration by any convenient route. Such compositions are preferably in a form adapted for use in medicine, in particular human medicine, and can conveniently be formulated in conventional manner using one or more pharmaceutically acceptable carriers for excipients.

In a further aspect there is provided a compound of formula (I) or salt or solvate thereof for use in therapy, in particular in human medicine. It will be appreciated that use in therapy embraces but is not necessarily limited to use of a compound of formula (I) or a salt or solvate thereof as an active therapeutic substance.

There is also provided as a further aspect of the invention the use of a compound of formula (I) in the preparation of a medicament for use in the treatment of conditions associated with cephalic pain such as cluster headache, chronic paroxysmal hemicrania, headache associated with vascular disorders, headache associated with substances or their withdrawal (for example drug withdrawal), tension headache and in particular migraine.

In an alternative or further aspect there is provided a method for the treatment of a mammal, including man, comprising administration of an effective amount of a compound of formula (I) or salt or solvate thereof in particular in the treatment of conditions associated with cephalic pain and in alleviating the symptoms associated therewith.

It will be appreciated that reference to treatment is intended to include prophylaxis as well as the alleviation of established symptoms. Compounds according to the invention may be administered as the raw chemical but the active ingredient is preferably present as a pharmaceutical formulation.

The active ingredient may conveniently be presented in unit dose form. A convenient unit dose formulation contains the active ingredient compound in an amount of from 0.1 mg to 100 mg.

The compounds according to the invention may for example be formulated for oral, sub-lingual, buccal, parenteral, rectal or intranasal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium sterate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl-p-hydroxybenzoates or sorbic acid).

Tablets for sub-lingual administration may be formulated in a similar manner to those for oral administration.

For buccal administration the compositions may take the form of tablets or lozenges formulated in conventional manner.

The compounds of the invention may be formulated for parenteral administration by injection, conveniently intravenous or subcutaneous injection, for example by bolus injection or continuous intravenous infusion. Formulations for injection may be presented in unit dosage from e.g. in ampoules or in multi-dose containers, with an added preservative.

The compositions may take such forms as suspension, solutions or emulsions in oily or aqueous vehicles, and may contain formulatory agents such as suspending, stabilising and/or dispersion agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glyceride.

For intranasal administration the compounds of the invention may be used, for example, as a liquid spray or powder or in the form of drops.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin or use in an inhaler or insufflator may be formulated containing a powder mix of a compound of the invention and a suitable powder base such as lactose or starch.

It will be appreciated that the precise dose administered will depend on the age and condition of the patient, the particular compound used and the frequency and route of administration. The compound may be administered in single or divided doses and may be administered one or more times, for example 1 to 4 times per day.

A proposed dose of the compounds of the invention for oral, sub-lingual, parenteral, buccal, rectal or intranasal administration to man (of approximately 70 kg bodyweight) for the treatment of migraine if 0.1 to 100 mg of the active ingredient per unit dose which could be administered, for example, 1 to 4 times per day.

For oral administration a unit dose will preferably contain from 2 to 100 mg for example 50 mg of the active ingredient. A unit dose for parenteral administration will preferably contain 0.2 to 5 mg of the active ingredient.

Aerosol formulations are preferably arranged so that each metered dose or 'puff' delivered from a pressurised aerosol contains 0.2 mg to 2 mg of a compound of the invention, and capsules and cartridges delivered from an insufflator or an inhaler, contain 0.2 mg to 20 mg or a compound of the invention. The overall daily dose by inhalation with an aerosol will be within the range 1 mg to 250 mg. Administration may be several times daily, for example from 2 to 8 times, giving for example 1, 2 or 3 doses each time.

Dosages of the compounds of the invention for rectal and sub-lingual are similar to those for oral administration. For intranasal administration a unit dose will preferably contain from 10 to 100 mg of the active ingredient.

The compounds of the invention may, if desired, be administered in combination with one or more other therapeutic agents, such as analgesics, anti-inflammatory agents and anti-nauseants, and formulated for administration by any convenient route in conventional manner. Appropriate doses will be readily appreciated by those skilled in the art.

According to another aspect of the invention, compounds of general formula (I) and physiologically acceptable salts and solvents (e.g. hydrates) thereof, may be prepared by the general methods outlined below. In the following processes, $R_1$, $R_2$, $R_3$; $R_6$ and n are as defined for the general formula (I) unless otherwise specified.

According to one general process (A), a compound of formula (I) wherein $R_1$ represents $R_4R_5NSO_2$— or $R_4R_5NCO$— may be prepared by condensing an amine of formula $R_4R_5NH$ with an acid of general formula (II)

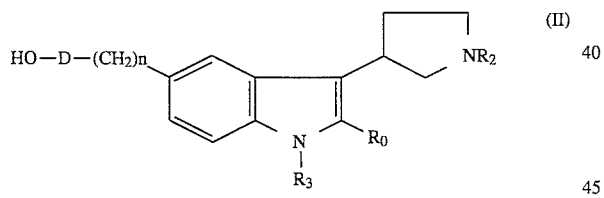

(wherein D represents —CO— or —SO$_2$—) or an acylating or sulphonylating agent corresponding thereto, or a salt (for example, an organic or inorganic acid addition saltsuch as the hydrochloride, hydrobromide, maleate, sulphate or creatinine sulphate adduct) or a protected derivative thereof.

Acylating agents corresponding to the acid of general formula (II) which may conveniently be used in the above process include acid halides (for example carboxylic acid chlorides and sulphonyl chlorides), alkyl esters (for example the methyl or ethyl esters), activated esters (for example, the 2-(1-methylpyridinyl)ester), mixed anhydrides (for example, diphenylcarbamic anhydride or pivalic anhydride), or other activated carboxylic acid derivatives such as those conveniently used in peptide synthesis.

The condensation process involving the acylating agents may be effected in a suitable reaction medium which may be aqueous or non-aqueous and conveniently at a temperature of from −70° to +150° C. Thus the condensation reaction using an acid halide, anhydride or activated ester may be effected in a suitable reaction medium such as an amide (e.g. N,N'-dimethylformamide), an ether (e.g. tetrahydrofuran), a nitrile (e.g. acetonitrile), a haloalkane (e.g. dichloromethane) or mixtures thereof, optionally in the presence of a base such as pyridine or triethylamine or an inorganic base such as sodium carbonate or sodium bicarbonate. The condensation reaction using an alkyl ester may be effected in a suitable reaction medium such as an alcohol (e.g. methanol), an amide (e.g. dimethylformamide), an ether (e.g. tetrahydrofuran) or mixtures thereof and conveniently at a temperature of from 0° to 100° C. In some instances, the amine $R_4R_5NH$ may itself act as reaction solvent.

The reaction involving condensation of an amine $R_4R_5NH$ with a carboxylic acid of general formula (II) is desirably conducted in the presence of a coupling agent such as carbonyl diimidazole or N,N'-dicyclohexylcarbodiimide. The condensation reaction may be carried out in a suitable reaction medium such as an ether (for example, tetrahydrofuran), a haloalkane (for example, dichloromethane), a nitrile (for example, acetonitrile) or an amide (for example, dimethylformamide) conveniently at a temperature of from −5° to +30° C. The reaction may also be carried out in the absence of a coupling agent in a suitable reaction medium such as a hydrocarbon (for example, toluene or xylene) conveniently at a temperature of from 50° to 120° C.

Where it is desired to prepare a compound of formula (I) in which $R_4$ and $R_5$ are both hydrogen atoms, ammonia may be used in the from of aqueous ammonia or in a solvent such as methanol.

Compounds of formula (II) or acylating agents corresponding thereto may be prepared by methods analogous to those described in UK Patent Specification 2035310 and 'A Chemistry of Heterocyclic Compounds—Indoles Part II', Chapter VI, edited by W. J. Houlihan (1972) Wiley Interscience, New York.

For example, compounds of formula (II) wherein n is zero may conveniently be prepared from the corresponding 5-bromo substituted compound of formula (III)

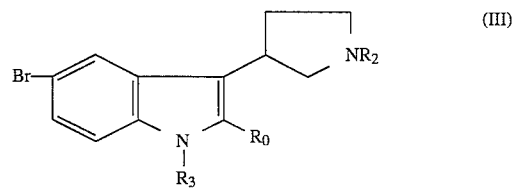

by conventional carboxylation by treatment with carbon dioxide in the presence of an alkyl lithium such as sec-butyl lithium. Compounds of formula (III) may themselves be prepared by reacting 5-bromoisatin with an appropriate pyrrolidinone in the presence of a base such as lithium diisopropylamide in an inert solvent such as tetrahydrofuran followed by reduction of the resulting intermediate indole-2-one with a reducing agent such as lithium aluminium hydride and dehydration in the presence of a catalytic amount of a organic acid such as 4-toluenesulphoic acid.

According to another process (B) a compound of formula (I) wherein $R_1$ represents $R_4CONH$— or $R_4SO_2NH$— may be prepared by condensing an amine of formula (IV)

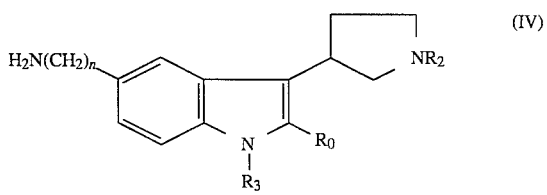

or a protected derivative thereof with an acid of formula $R_4DOH$ (wherein D represents —CO— or —SO$_2$—) or an acylating agent corresponding thereto or a salt or protected derivative thereof.

Suitable acylating agents which may conveniently be used in the above process include acid halides (for example carboxylic acid chlorides and sulphonyl chlorides), alkyl esters and activated esters (for example diphenylcarbamic anhydride or pivalic anhydride). The reaction is conveniently effected in a reaction medium and at a temperature as described for process (A) above.

Compounds of formula (IV) may be prepared, for example, by reduction of a corresponding compound having an appropriate reducible group as the 5-position substituent, such as —(CH$_2$)xCN or —(CH$_2$)xCONH$_2$ wherein x is zero, or 1 to 4 using for example lithium aluminium hydride. Compounds of formula (IV) wherein n is zero may be prepared by reduction of the corresponding 5-nitro compound using, for example, lithium aluminium hydride or catalytic hydrogenation.

According to another general process (C), compounds of formula (I) may be prepared by cyclisation of a compound formula (V)

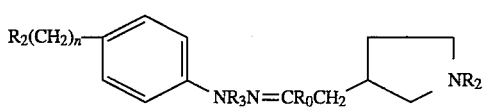

(V)

The processes is desirably carried out in the presence of polyphosphate ester in a reaction medium which may comprise of one of more organic solvents, preferably halogenated hydrocarbons such as chloroform, dichloromethane, dichloroethane, dichlorodifluoromethane, or mixtures thereof. Polyphosphate ester is a mixture of esters which may be prepared from phosphorous pentoxide, diethylether and chloroform according to the method described in 'Reagents for Organic Synthesis', (Fieser and Fieser, John Wiley and Sons 1967).

Alternatively the cyclisation may be carried out in aqueous or non-aqueous media, in the presence of an acid catalyst. When an aqueous medium is employed this may be an aqueous organic solvent such as an alcohol (e.g. methanol, ethanol or isopropanol) or an aqueous ether (e.g. dioxan or tetrahydrofuran) as well as mixtures of such solvents and the acid catalyst may be for example in inorganic acid such as concentrated hydrochloric polyphosphoric or sulphuric acid. (In some cases the acid catalyst may also act as the reaction solvent). In an anhydrous reaction medium, which may comprise one or more alcohols or ethers (e.g. as described above) or esters (e.g. ethyl acetate), the acid catalyst will generally be a Lewis acid such as boron trifluoride or zinc or magnesium chloride. The cyclisation reaction may conveniently be carried out at temperatures of from 20° to 200° C. preferably 50° to 125° C.

According to a particular embodiment of this process, compounds of general formula (I) may be prepared directly by the reaction of a compound of general formula (VI):

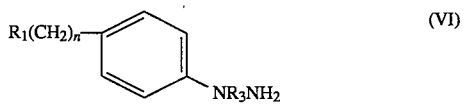

(VI)

or a salt thereof, with a compound of formula (VII):

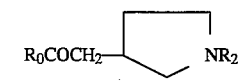

(VII)

or a salt or protected derivative thereof (such as an acetal e.g. formed with an appropriate allkylorthoformate), using the appropriate conditions as described above. It will be appreciated that in this embodiment a compound of formula (V) is formed as an intermediate and may be reacted in situ to form the desired compound of formula (I).

Compounds of the general formula (V) may be isolated as intermediates during the process for the preparation of compounds of general formula (I) wherein a compound of formula (VI), or a salt thereof, is reacted with a compound of formula (VII) or a salt or protected derivative thereof, in a suitable solvent such as an aqueous alcohol (e.g. methanol) and at a temperature of, for example, from 20° to 100° C. If an acetal of a compound of formula (VII) is used it may be necessary to carry out the reaction in the presence of an acid (for example, acetic or hydrochloric acid). In some cases the acid may also act as the reaction solvent.

Compounds of general formula (VI) may be prepared in a number of conventional steps from compounds of formula (VIII)

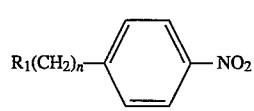

(VIII)

For example, a compound of formula (VIII) may be reduced by catalytic dehydrogenation using a catalyst such as palladium on charcoal to give an amine which may be diazotised using, for example nitrous acid. The product of this reaction may then be reduced using, for example, stannous chloride, to give a compound of formula (VI).

According to another general process (D), a compound of formula (I) wherein n represents 2 to 5 may be prepared by reduction of a compound of formula (IX)

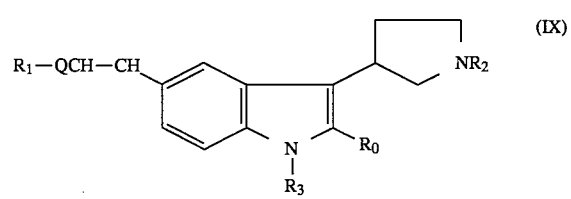

(IX)

(wherein —QCH=CH represents a $C_{2-5}$ alkenyl chain).

The reduction may be effected by methods well known in the art. Thus, for example, a compound of formula (IX) may be reduced by catalyic hydrogenation using a heterogeneous or homogeneous catalyst. Heterogeneous catalysts which may be employed include Raney nickel, and nobel metal catalysts such as platinum, platinum oxide, palladium, palladium oxide, rhodium or ruthenium which may be supported for example on charcoal kieselguhr or alumina. In the case of Raney nickel, hydrazine may also be used as the source of hydrogen. Alternatively a homogeneous catalyst such as tris(triphenylphosphine) rhodium chloride may be used. The catalytic hydrogenation may conveniently be carried out in a solvent such as an alcohol, for example ethanol; an ether, for example dioxan or tetrahydrofuran; an amide, for example dimethylformamide or an ester, such as ethyl acetate, and at a temperature of from −10° to +50° C. preferably ⁻5 ° to +30° C.

Compounds of formula (IX) may be prepared by reacting a compound of formula (X)

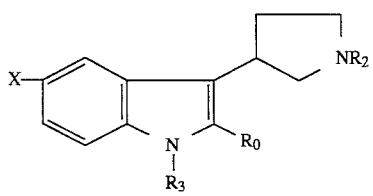

(wherein X represents a leaving atom or group such as a halogen atom for example a bromine atom) with an alkene $R_1QCH=CH_2$.

The reaction will generally be effected in the presence of a palladium catalyst and a base. The catalyst may be, for example, palladium on charcoal or a palladium salt. Palladium salts which may be employed as catalysts include salts of organic acids such as acetates or salts or inorganic acids such as chlorides or bromides. The base may be, for example, a tertiary nitrogen base such has triethylamine or tri-n-butylamine or an alkali metal carbonate such as sodium carbonate. The reaction may optionally be carried out in the presence of a phosphine, for example a triarylphosphine such as triphenylphosphine or tri-o-tolylphosphine. A phosphine should be present when the process is effected with a compound of formula (X) wherein X represents a bromine atom.

General process (D) may be effected in the presence of solvent. An anhydrous or aqueous reaction medium comprising one or more solvents may be employed. Suitable solvents include nitriles, for example, acetonitrile, alcohols, for example methanol, amides, for example dimethylformamide, N-methylpyrrolidine or hexamethylphosphoramide; and water. The reaction may conveniently be carried out at a temperature of from 25° to 200° C., preferably 75° to 150° C.

Compounds of formula (X) may be prepared from known compounds by methods analogous to those described herein.

According to another general process (E) a compound of formula (I) according to the invention may be converted into another compound of the invention using conventional procedures.

According to one embodiment of this process, a compound of general formula (I) wherein $R_2$ is a hydrogen atom, may be prepared by reduction of a corresponding compound of general formula (I) wherein $R_2$ is a benzyl group, for example with hydrogen in the presence of a catalyst e.g. 10% palladium on charcoal.

According to another embodiment of general process (E), a compound of formula (I) wherein one or more of $R_2$, $R_3$ and $R_0$ represent hydrogen atoms may be alkylated using conventional techniques. It will be understood that the term 'alkylation' embraces the introduction of an alkyl, alkenyl or phenylalkyl group. The reaction may be effected using a suitable alkylating agent such as an alkyl halide, alkyl tosylate or dialkylsulphate. The alkylation reaction may conveniently be carried out in an inert organic solvent such as an amide (e.g. dimethylformamide) or an ether (e.g. tetrahydrofuran) preferably in the presence of a base. Suitable bases include, for example, alkali metal hydrides, such as sodium hydride, alkali metal carbonates, such as sodium carbonate or alkali metal alkoxides such as sodium or potassium methoxide, ethoxide or t-butoxide. The alkylation reaction is conveniently carried out at a temperature of from 0° to 100° C.

According to a still further embodiment, a compound of general formula (I) in which $R_3$ represents a group $-CO_2R_6$, $-COR_6$, $-COCOR_6$ or $-CONHR_6$ may be prepared by acylating the corresponding compound of formula (I) wherein $R_3$ represents a hydrogen atom, or a protected derivative thereof. Acylating agents corresponding to the group $R_3$ which may be used in this general process include acid halides (e.g. acid chlorides such as acetyl chloride); alkyl haloformates (e.g. methyl or ethyl chloroformate); mixed or symmetrical anhydrides (e.g. acetic anhydride or benzoic anhydride); carbonates (e.g. diethyl carbonate); and isocyanates (e.g. methyl isocyanate).

The reaction is conveniently effected in the presence of a base, such as an alkali metal hydride, e.g. sodium or potassium hydride; an alkali metal carbonate e.g. sodium or potassium carbonate; and alkali metal alkoxide e.g. potassium t-butoxide; butyllithium; or an organic teriary amine, e.g. triethylamine, or pyridine. Suitable solvents which may be employed in the acylation process include amides e.g. dimethylformamide, or dimethylacetamide; ethers, e.g. tetrahydrofuran or dioxan; halogenated hydrocarbons e.g. methylene chloride; nitriles e.g. acetonitrile and esters e.g. ethyl acetate. The reaction may conveniently be effected at a temperature in the range −10° to +150° C.

Alternatively the acylation may be effected in a two-phase reaction medium, in the presence of a phase transfer catalyst, such as tetrabutylammonium hydrogen sulphate or tetraethylammonium bromide. Thus for example the acylating agent may be reacted with a compound of formula (I) in an inert organic solvent (e.g. a halogenated hydrocarbon such as methylene chloride), and an aqueous solution of a base (e.g. 50% sodium hydroxide) containing a phase transfer catalyst.

It will be appreciated that in compound of general formula (I) wherein $R_2$ represents hydrogen it will be necessary to protect the group $NR_2$ during the acylation process. Suitable protecting groups which may be used include conventional amino protecting groups as described for general process (G) hereinafter.

According to another general process (F), a compound of formula (I) may be prepared by reduction of a compound of formula (XI)

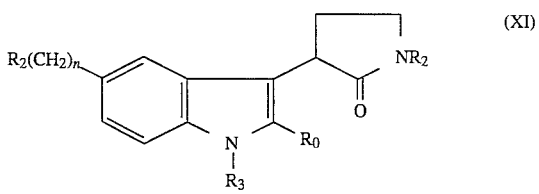

The reaction may conveniently be effected using a hydride reducing agent, such as a metal hydride, e.g. lithium aluminium hydride or sodium borohydride or diborane, in a suitable solvent, such as and ether, e.g. tetrahydrofuran, dioxan or diethyl ether at a temperature of from 0° to 110° C., preferably at about 70° C.

Compounds of formula (XI) may be prepared by reaction of a compound of formula (VI), or a salt thereof, with a compound of formula (XII)

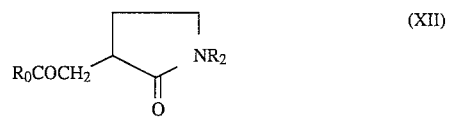

as described in process (C) above.

Compounds of formula (XII) may be prepared from the corresponding alcohol of formula (XIII)

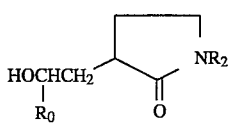

(XIII)

by oxidation, for example using dimethylsulphoxide and oxalyl chloride in dichloromethane, followed by treatment with triethylamine, which reaction is preferably effected at a temperature of from −75° to 0° C., or chromic acid in water, aqueous acetic acid or aqueous acetone, preferably at room temperature.

According to another general process (G), a compound of general formula (I) according to the invention, or a salt thereof may be prepared by subjecting a protected derivative of general formula (I) or a salt thereof to reaction to remove the protecting group or groups.

Thus, at an earlier stage in the preparation of a compound of general formula (I) or a salt thereof it may have been necessary and/or desirable to protect one or more sensitive groups in the molecule to prevent undesirable side reactions.

The protecting groups used in the preparation of compounds of formula (I) may be used in conventional manner. See for example 'Protective Groups in Organic Chemistry' Ed. J. F. W. McOmie (Paragim Press 1973) or 'Protective Groups in Organic Synthesis' by Theodora W. Greene (John Wiley and Sons 1981).

In compounds of general formula (I) wherein $R_2$ represents hydrogen the group $NR_2$ may be protected for example by protonation or with a conventional amino protecting group. Such groups may include for example aralky groups, such as benzyl, diphenylmethyl or triphenylmethyl groups; and acyl groups such as N-benzloxycarbonyl or t-butoxycarbonyl. The indole nitrogen may also be protected, for example by an aralky group such as benzyl.

Removal of any amino protecting groups present may be achieved by conventional procedures. Thus an aralkyl group such as benzyl, may be cleaved by hydrogenolysis in the presence of a catalyst (e.g. palladium on charcoal); an acyl group such as N-benzyloxycarbonyl may be removed by hydrolysis with, for example, hydrogen bromide in acetic acid or by reduction, for example by catalytic hydrogenation.

As will be appreciated, in some of the general processes (A) to (F) described above it may be necessary or desired to protect any sensitive groups in the molecule as just described. Thus, a reaction step involving deprotection of a protected derivative of general formula (I) or a salt thereof may be carried out subsequent to any of the above described processes (A) to (F).

Thus, according to a further aspect of the invention, the following reactions may, if necessary and/or desired be carried out in any appropriate sequence subsequent to any of the processes (A) to (F).

(i) removal of any protecting groups; and (ii) conversion of a compound of general formula (I) or a salt thereof into a physiologically acceptable salt thereof.

Where it is desired to isolate a compound of the invention as a salt, for example as an acid addition salt, this may be achieved by treating the free base of general formula (I) with an appropriate acid, preferably with an equivalent amount.

When a specific enatiomer of a compound of formula (I) is required, this may be obtained by resolution of a corresponding racemate of a compound of formula (I) using conventional methods.

As well as being employed as the last main step in the preparative sequence, the general methods indicated above for the preparation of the compounds of the invention may also be used for the introduction of the desired groups at an intermediate stage in the preparation of the required compound. It should therefore be appreciated that in such multi-stage processes, the sequence of reactions should be chosen in order that the reaction conditions do not affect groups present in the molecule which are desired in the final product.

The invention is further illustrated by the following non-limiting Examples. All temperatures are in °C. Solutions were dried with $Na_2SO_4$ unless otherwise indicated. Chromatography was carried out by flash chromatography on silica (Merck 9385) unless otherwise stated. Ammonia and $NH_3$ as used refer to 0.88 aqueous ammonia.

EXAMPLE 1

N-Methyl-3-(1-methyl-3-pyrrolidinyl)-1H-indole-5-ethanesulphonamide hydrochloride 5-Bromo-1,3-dihydro-3-hydroxy-3-(1-methyl-2-oxo-3-pyrrolidinyl)-1H-indol-2-one Lithium diisopropylamide [prepared by adding n-butyllithium (1.6 Molar solution in hexanes, 32.0 ml, 51.4 mmol) in a stream to a solution of diisopropylamine (5.05 g, 50 mmol) in dry, freshly distilled tetrahydrofuran (80 ml) at −78°, warming the resultant solution slowly to −10° then cooling again to −78°] was added in a stream to a stirred solution of 5-bromoisatin (5.65 g, 25.0 mmol) and N-methypyrrolidinone (2,48 g, 25.0 mmol) in dry, freshly distilled tetrahydrofuran (110 ml) at 10°0 (ice-water bath), with stirring, under nitrogen. The temperature of the mixture dropped to ca 0° after the addition was complete and the colour of the reaction mixture became almost black. The mixture was warmed slowly to room temperature, with stirring, and stirred at room temperature for 3 h. The mixture was left at 0° over the weekend, then cautiously added to 2N hydrochloric acid (200 ml). The phases were separated. The aqueous phase was extracted with ethyl acetate (3×200 ml). The combined organics were washed with saturated brine (200 ml), dried and evaporated to give a gum (8.4 g). The gum was chromatographed on silica (400 g), using a mixture of ethyl acetate and methanol (40:1) as the eluant, to give a semi-solid (4 g). The material was heated in ethyl acetate (ca 80 ml) on a steam-bath for 10 min. The suspension was filtered and the solid dried to give the product (3.51) as a powder, m.p. 189°–194°.

Analysis Found: C,48.2; H,4.1; N,8.4; Br, 24.3.

$C_{13}H_{13}BrN_2O_3$ requires C,48.0; H,4.0; N,8.6; Br, 24.6%.

5-Bromo-3-(1-methyl-3-pyrrolidinyl)1-H-indole

A solution of the product of stage (i) (mixture of diastereoisomers, 3.08 g) in dry tetrahydrofuran (210 ml) was added in a stream over 10 min to a suspension of lithium aluminium hydride (2.90 g, 76.7 mmol) in dry tetrahydrofuran (100 ml ) at 5°, under nitrogen, with stirring (air stirrer). The ice-bath was removed, the mixture was heated to reflux over 1 h then heated at reflux for a further 18 h. The mixture was cooled to 5°, with stirring, and cautiously treated with a mixture of water (15 ml) and tetrahydrofuran (80 ml). The resultant mixture was filtered and the residue was washed well with ethanol. The combined filtrate and washings were evaporated to give a semi-solid, which was heated in a mixture of ethyl acetate and methanol (ca 10:1; 100 ml) on a steam bath for 5 min then filtered. The filtrate was evaporated to give a gum (2.9 g). The gum was dissolved in toluene (200 ml). 4-Toluenesulphonic acid (252 mg, 1.321 mmol) was added and the mixture was heated at reflux, with stirring, over 4 molecular sieves of 2 h. More 4-toluensulphonic acid (280 mg, 1.47 mmol) was added and the mixture was refluxed for a further 2 h; filtered and the filtrate evaporated. The residue was partitioned between ethyl acetate (200 ml) and 2N sodium carbonate (80 ml). The aqueous phase was separated and extracted with ethyl acetate (100 ml). The combined organics were dried and evaporated to give an oil, which rapidly crystallised. The crystals were triturated with ether then dried in vacuo to give the indole (0.96 g) as a powder, with m.p. 146°–147°.

T.l.c. $SiO_2(CH_2Cl_2:EtOH:NH_3$ 50:8:1). Product has Rf 0.63.

(iii) (E)-N-Methyl-2-[3-(1-methyl-3-pyrrolidinyl)-1H-indol-5-yl]ethenesulphonamide A mixture of the product of stage (ii) (700 mg), N-methylethenesulphonamide (385 mg), palladium acetate (37 mg) tri-o-tolyl phospine (183 mg) and triethylamine (505 mg) in dimethylformamide (8 ml) was stirred and heated at 105° for 2 h. The mixture was cooled and the solvent was evaporated in vacuo. The residue was chromatographed on silica (Merck 9385; 110 g), using a mixture of dichloromethane, ethanol and ammonia (50:8:1) as the eluent, to give a gum (485 mg). The material was rechromatograped on silica (Merck 9385, 45 g), using a mixture of ethyl acetate, ethanol and ammonia (50:8:1) as the eluent, to give the sulphonamide (318 mg) as a white foam.

T.l.c. $SiO_2$ $(CH_2Cl_2:EtOH:NH_3$ 50:8:1) Rf 0.25

(iv) N-Methyl-3-(1-methyl-3-pyrrolidinyl)-1H-indole-5-ethanesulphonamide hydrochloride A solution of the product of stage (iii) (290 mg) in ethanol (35 ml) and 2N hydrochlorice acid (1 ml) was hydrogenated at room temperature and atmospheric pressure, using 10% palladium on carbon (580 mg, 50% w/w with $H_2O$) as the catalyst. After 1 h, when 20.6 ml (0.84 mmol) of hydrogen had been absorbed, the reaction was stopped. The mixture was filtered and was washed well with ethanol. The combined filtrate and washings were evaporated to give a gum. Attempts to crystallise the gum from a number of solvents were unsuccessful. The gum was dissolved in methanol (3 ml). The solution was cooled to 5°, with stirring, and treated dropwise with ether (100 ml) over 10 min. The solvents were decanted from the gummy residue, which was triturated with more ether (2×100 ml) over 4 h. (2 h+2 h). The solvent was decanted from the resultant solid which was dried in vacuo to give the hydrochloride (185 mg) as an amorphous solid, with m.p.> 70° (foams) (Shrinks between 50°–60°).
Analysis Found: C,51.5; H,7.1; N,10.9; Cl,9.6.

$C_{16}H_{23}N_3O_2S.HCl.0.8H_2O$ requires C,51.6; H,6.9; N,11.3; Cl,9.5%.

EXAMPLE 2

3-(1-Methyl-3-pyrrolidinyl)-1H-indole-5-carboxamide (i) (3-(1-Methyl-3-pyrrolidinyl)-1H-indole-5-carboxylic acid A solution of sec-butyllithium in cyclohexane (1.3M; 35 ml, 45.5 mmol) was added in a stream via a syringe to a stirred solution of the product of Example 1 stage (ii) (1.61 g) in dry, freshly-distilled tetrahydrofuran (110 ml) at −78°, under nitrogen. The mixture was stirred at −78° for 1 h then solid carbon dioxide (10 g) was added. The resultant suspension was then warmed to room temperature and stirred at room temperature for 2 h. Water (ca 20 ml) was cautiously added over 10 min, with ice-bath cooling. The solvents were evaporated. The residue was taken up in ethanol (2×30 ml). In each case the solvent was then removed in vacuo. The resultant semi-solid was chromatographed on silica (100 g), using a mixture of dichloromethane, ethanol and ammonia (10:10:1) as the eluant. Fractions containing the product were combined and evaporated to give the title compound (1.05 g) as a foam.

T.l.c. $SiO_2(CH_2Cl_2:EtOH:NH_3$ 10:10:1)Rf 0.05.

(ii) 3-(1-Methyl-3-pyrrolidinyl)-1H-indole-5-carboxamide

Oxalyl chloride (291 mg) was added dropwise to a stirred suspension of the product of stage (i) (340 mg) in dichloromethane (8 ml) and dimethylformamide (2 ml) at 5°, under nitrogen, with vigorous stirring. A clear solution was formed after ca 5 min. Stirring was maintained at 5° for 20 min. More oxalyl chloride (0.2 ml., 2.29 mmol) was added. The solution was stirred and warmed to room temperature over 20 min then added, using a pasteur pipette, to vigorously stirred ammonia (S.G. 0.88; aqueous solution; 6 ml) at 5°; under nitrogen. The mixture was stirred and warmed to room temperature over 00.75 h. The solvents were evaporated. The residue was dissolved in ethanol (35 ml). The solvent was again evaporated. The residue was chromatographed using a mixture of dichloromethane, ethanol and ammonia (12:8:1) as the eluant, to give the title compound (220 mg) as a gum, which foamed when further dried.

N.m.r. Contains methanol (0.2 Molar equiv.)

Analysis Found: C,65.3; H,7.0; N, 16.3.

$C_{14}H_{17}N_3O0.2MeOH.0.5H_2O$ requires C,65.7; H,7.3; N,16.2%.

T.l.c. $SiO_2$ $(CH_2Cl_2:EtOH:NH_3$ 12:8:1) Rf 0.4.

M.p. 70°–75° (shrinks).

EXAMPLE 3

N-[[3-(1-Methyl-3-pyrrolidinyl)-1H-indole-5-yl]methyl]methanesulphonamide hydrochloride 3-(1-Methyl-3-pyrrolidinyl)-1H-indole-5-methanamine A suspension of Example 2 (390 mg) in dry, distilled tetrahydrofuran (40 ml) was added cautiously to a stirred suspension of lithium aluminium hydride (300 mg, 8.00 mmol) in dry tetrahydrofuran (20 ml) at 5°, under nitrogen. The resultant suspension was stirred and heated at reflux for 3 h; cooled to 5° and cautiously treated with a mixture of water (3 ml) and tetrahydrofuran (12 ml), dropwise with vigorous stirring. Methanol (10 ml) was added. The solvents were evaporated to give a solid. The solid was combined with a sample from an identical small-scale reaction which had been carried out on 60 mg of the carboxamide of Example 2 and chromatographed on silica (28 g), using a mixture of dichloromethane, ethanol and ammonia (20:8:1) as the eluant, to give the title compound (323 mg) as a gum.

T.l.c. $SiO_2$ $(CH_2Cl_2:EtOH:NH_3$ 10:8:1). Rf 0.13.

N-[[3-(1-Methyl-3-pyrrolidinyl)-1H-indole-5-yl]methyl methane sulphonamide hydrochloride A solution of methanesulphonyl chloride (145 mg, 1.27 mmol) in dichloromethane (3 ml) was added drop wise to a vigorously stirred solution of the product of stage (i) (290 mg, 1.27 mmol) and triethylamine (290 mg, 2.87 mmol) in dry dichloromethane (15 ml) at 5°. The mixture was stirred and warmed to room temperature over 1 h. Dimethylformamide (4 ml) was added to dissolve some precipitated solid.

The mixture was stirred at room temperature for a further 0.5 h then the solvents were evaporated, using ethanol to remove the last traces of dimethyformamide by azeotropic distillation. The residue was chromatographed on silica (30 g), using a mixture of dichloromethane, ethanol and ammonia (30:8:1) as the eluant, to give the free base of the product (231 mg) as a clear gum.

T.l.c. $SiO_2$ ($CH_2Cl_2$:EtOH:$NH_3$ 30:8:1) Rf 0.5. U.v., $KMnO_4$, IPA detection.

Methanolic hydrogen chloride [prepared by adding acetyl chloride (110 mg, 1.40 mmol) to methanol (3 ml) with stirring] was cooled to 5° and added dropwise to a solution of the product (free base) (221 mg, 0.72 mmol) in a mixture of ethyl acetate (15 ml) and methanol (1 ml) at 5°, with stirring. The resultant clear solution was treated dropwise with ethyl acetate (40 ml), with stirring. A gum was precipitated. The solvents were decanted from the gum which was triturated in ethyl acetate (2×50 ml) over 4 h. (2 h+2 h). The solvent was decanted from the resultant solid precipitate, which was dried in vacuo to give the hydrochloride (196 mg) as a powder, with m.p. 142°–146°.

Analysis Found: C51.9; H,6.15; N,11.7; Cl,10.5.

$C_{15}H_{21}N_3O_2S.HCl.0.13H_2O$ requires C,52.0; H,6.5; N,12.1; Cl, 10.2%.

Water Analysis Contains 0.38% $H_2O$ w/w.

EXAMPLE 4

N-Methyl-3-(1-methyl-3-pyrrolidinyl)-1H-indole-5-methanesulphonamide (i) 1-Methyl-3-(2-oxoethyl)-2-pyrrolidinone A solution of dimethylsulphoxide (1.7 ml) in dichloromethane (10 ml) was added dropwise over 5 min to a stirred solution of oxalyl chloride (1.0 ml) in dichloromethane (20 ml) at −72° under nitrogen. The resultant solution was stirred at −72° for 5 min then a suspension of 3-(2-hydroxyethyl)-1-methyl-2-pyrrolidinone (1.30 g) in dichloromethane (10 ml) and dimethylsulphoxide (1 ml; added to improve dissolution of the alcohol) was added dropwise over 8 min. The resultant cloudy solution was stirred at −72° for 15 min then treated with triethylamine (7.0 ml). The resultant suspension was warmed to room temperature and stirred at room temperature for 1 h. The suspension was filtered. The residue was washed with ethyl acetate. The combined filtrate and washings were evaporated to give a semi-solid which was chromatographed using a mixture of ethyl acetate and methanol (5:1) as the eluent, to give the title compound (743 mg).

T.l.c. $SiO_2$ (EtOAc:MeOH 5:1). Rf 0.55.

(ii) N-Methyl-3-(1-methyl-2-oxo-3-pyrrolidinyl)-1H-indole-5-methanesulphonamide

A solution of the product of stage (i) (692 mg) in ethanol (40 ml) was added to a suspension of 4-hydrazino-N-methylbenzenemethanesulphonamide hydrochloride (1.47 g) and sodium acetate trihydrate (1.18 g) in water (30 ml) and ethanol (20 ml). The resultant solution was stirred at room temperature for 1 h then concentrated to ca 40 ml in vacuo. Water (50 ml) was added and the mixture was extracted with ethyl acetate (3×70 ml). The combined organics were dried and evaporated to give the intermediate hydrazone (1.47 g) as a pale yellow gum.

A solution of the hydrazone (1.47 g) in chloroform (50 ml) was treated, at room temperature with stirring, with a solution of polyphosphate ester ("PPE", 8.00 g) in chloroform (30 ml). The resultant solution was stirred and heated at 60°–65°, under nitrogen, for 1.25 h. The mixture was cooled to 5°, with stirring, and treated with 8% sodium bicarbonate (70 ml). When gas evolution had ceased, stirred was stopped and the phases were separated. The aqueous phase was extracted with chloroform (2×70 ml). The combined organics were washed with 8% sodium bicarbonate (100 ml), dried and evaporated to give a dark gum (2.05 g). The gum was chromatographed using a mixture of ethyl acetate and methanol (6:1) as the eluent, to give a resinous, yellow gum (0.95 g). The gum was dissolved in a mixture of methanol (ca 6 ml) and water (ca 14 ml). The mixture was saturated with potassium carbonate, left to stand for 15 min then extracted with ethyl acetate (2×30 ml). The combined organics were dried and evaporated to give a foam (700 mg). The foam was chromatographed using a mixture of ethyl acetate and methanol (6.1) as the eluent, to give the title compound (617 mg) as a pale yellow foam.

T.l.c. $SiO_2$ (EtOAc:MeOH 6.1). Rf 0.55.

Analysis Found: C54.7; H,5.9; N,12.6.

$C_{15}H_{19}N_3O_3S.0.5H_2O$ requires: C,54.5; H,6.1; N,12.7%.

(iii) N-Methyl-3-(1-methyl-3-pyrrolidinyl)-1H-indole-5-methanesulphonamide

A solution of the product of stage (ii) (450 mg) in dry tetrahydrofuran (20 ml) was added cautiously to a stirred suspension of lithium aluminium hydride (200 mg) in dry, freshly distilled tetrahydrofuran (20 ml) at 5°, under nitrogen. The reaction mixture was stirred and heated at reflux for 1 h; cooled to 5°, with stirring, and cautiously treated with a mixture of tetrahydrofuran (6 ml) and water (1 ml). The mixture was filtered through "hyflo". The residue was washed with ethanol. The combined filtrate and washings were evaporated to give a gum which was crystallised from a mixture of ethyl acetate and ether. The product was partitioned between ethyl acetate (30 ml) and 8% sodium bicarbonate (30 ml). The aqueous phase was extracted with ethyl acetate (2×30 ml). The combined organics were dried and evaporated to give a gum, which was crystallised from a mixture of ethyl acetate and cychlohexane to give the title compound (190 mg) as a cream powder, with m.p. 160°–162°.

Analysis Found: C,58.8; H,6.8; N,13.2.

$C_{15}H_{21}N_3O_2S$ requires: C58.6; H,6.9; N,13.7%.

EXAMPLE 5

N-Methyl-3-(1-methyl-3-pyrrolidinyl)-1H-indole-5-propanesulphonamide hydrochloride salt (E)-N-Methyl-3-[3-(1-methyl-3-pyrrolidinyl)-1H-indol-5-yl]-2-propenesulphonamide A mixture of the product of Example 1(ii) (0.8 g), triethylamine (0.57 g), palladium II acetate (43 mg), tri-o-tolylphosphine (0.22 g), N-methyl-2-propenesulphonamide (530 mg) and dimethylformamide (48 ml) were heated together at 100° for 4h. More triethylamine (0.5 g), palladium II acetate (60 mg), tri-o-tolylphosphine (100 mg), N-methyl-2-propenesulphonamide (250 mg) were added to the reaction mixture, which was heated at 100° for a further 21 h. The reaction mixture was cooled to room temperature, and the solvent was evaporated in vacuo to give a brown residue. The residue was purified by chromatorgraphy using dichloromethane:ethaonl:ammonia (50:8:1) as eluant to give the title compound (490 mg).

Analysis Found: C59.9; H,6.6; N,11.5.

$C_{17}H_{23}N_3S.O22H_2O.0.2Ch_3OH$ requires C,60.1;H, 7.1; N, 12.2%

Water analysis contains 1.18% $H_2O$ w/w

T.l.c.$CH_2Cl_2$:EtOH:$NH_3$ (50:8:1), Rf 0.18.

(ii) N-Methyl-3-(1-methyl-3-pyrrolidinyl)-1H-indole-5-propanesulphonamide hydrochloride The product of stage (i) (450 mg) was dissolved in dimethylformamide (10 ml) and ethanol (20 ml). The solution was hydrogenated in the presence of Raney Nickel catalyst (900 mg) for 19 h at room temperature and pressure. The catalyst was filtered off and the solvent was evaporated in vacuo to leave a brown oil. The oil was purified by chromatography eluting with dichloromethane:ethanol:ammonia (50:8:1) to give the product as an oil (190 mg).

The oil (180 mg) was dissolved in ethanol (2 ml) and the solution was cooled to 0° C. Ethanolic hydrogen chloride (2 ml) was added with stirring and diethyl ether (10 ml) was added dropwise. The mixture was warmed to room temperature and was stirred for 2 h. The solvents were decanted and the solid hydrochloride was dried in vacuo for 2 h to give the title compound (187 mg).

Analysis Found: C53.7; H, 7.2; N, 10.6; Cl, 8.71;

$C_{18}H_{25}N_3SO_2.HCl.1.3H_2O.0.16C_4H_{10}O$ requires C, 53.7; H,7.2; N,10.6; Cl, 8.5%

Water analysis contains 2.15% $H_2O$ w/w

T.l.c. $CH_2Cl_2$:EtOH:$NH_3$ (50.8:1), Rf=0.18,

EXAMPLE 6

N-Methyl-3-(1-methyl-3-pyrrolidinyl)-1H-indole-5-acetamide hydrochloride (i) 1-Methyl-3-pyrrolidineethanol Lithium aluminium hydride (347 mg) was cautiously added, in portions, to a vigorously stirred suspension of 3-(2-hydroxyethyl)-1-methyl-2-pyrrolidinone (886 mg) in dry, freshly distilled tetrahydrofuran (60 ml), at 5° under nitrogen. The resultant suspension was stirred and heated at reflux under nitrogen for 1 h. The mixture was cooled to 5°, with stirring, and cautiously treated with a mixture of water (1 ml) and tetrahydrofuran (10 ml). The solvents were evaporated, the residue dissolved in ethanol and the solvent was again removed, in vacuo. The residue was chromatographed using dichloromethane:ethanol:ammonia (25.8:1) as eluent, to give the title compound (423 mg).

T.l.c ($CH_2Cl_2$:EtOH:$NH_3$ 25:8:1), Rf 0.3.

1-Methyl-3-pyrrolidineacetaldehyde

Dimethylsulphoxide (0.36 ml) was added dropwise to a solution of oxalyl chloride (0.33 ml) in dry dichloromethane (8 ml) at −72°, with stirring under nitrogen. The solution was stirred at −72° for 5 min then a solution of the compound of stage (i) (325 mg) in dry dichloromethane (5 ml) was added in a stream over 3 min. The solution was stirred at −72° for 15 min then triethylamine (1.75 ml) was added. The mixture was then warmed to room temperature over 1 h. The solvent and excess triethylamine were evaporated to give the crude title compound which was used immediately in the next step.

T.l.c. $CH_2Cl_2$:EtOH:$NH_3$ (25.8:1). Product streaks to Rf 0.2 (evidence for decomposition).

(iii) N-Methyl-3-(1-methyl-3-pyrrolidinyl)-1H-indole-5-acetamide hydrochloride

A solution of the product of stage (i) in ethanol (13 ml) was added in a stream to a solution of 4-hydrazino-N-methylbenzeneacetamide hydrochloride (431 mg) and sodium acetate trihydrate (544 mg) in water (12 ml) and ethanol (8 ml). The solution was stirred at room temperature for 0.75 h, concentrated a ca. 5 ml in vacuo, and sodium bicarbonate solution (8%, 40 ml) was added, followed by a small amount of solid potassium carbonate to saturate the solution. The solution was extracted with ethyl acetate (3×50 ml). The combined organics were dried and evaporated to give the intermediate hydrazone (480 mg) as a gum, which was used without further purification.

T.l.c. $CH_2Cl_2$:EtOH:$NH_3$ (25.8:1), Rf 0.5.

A solution of the crude hydrazone (480 mg) and polyphosphate ester (2.5 g) in chloroform (20 ml) was stirred and heated at 60°–65° under nitrogen for 1 h. The solution was cooled to 5° and ice (ca. 20 ml) was added, with stirring. The mixture was stirred vigorously for 10 min, solid potassium carbonate was added to saturate the aqueous phase, and stirring was maintained at 5° for 5 min. The phases were separated. The aqueous phase was extracted with chloroform (20 ml) and ethyl acetate (20 ml). The combined organics were dried and evaporated to give a viscous oil. The oil was chromatographed using dichloromethane:ethanol:ammonia (25:89:1) as eluant, to give the acetamide (free base) (92 mg) m.p. 44°–47°.

T.l.c. ($CH_2Cl_2$:EtOH:$NH_3$ 25:8:1), Rf 0.45.

The acetamide (free base: 70 mg) was partitioned between ethyl acetate (3 ml) and saturated sodium bicarbonate solution (1 ml). The aqueous phase was separated and extracted with ethyl acetate (8×3 ml). The combined organics were dried and filtered. The filtrate was cooled to 5°, with stirring, and cautiously treated with methanolic hydrogen chloride (ca. 0.5 molar solution) until the resultant suspension was just acidic. The mixture was stirred for 2 h. The solvents were decanted off and the precipitate, triturated in ether (50 ml) for 2 h. The solvent was decanted and the residue dried in vacuo to give the hydrochloride (63 mg).

T.l.c. as for the free base

Analysis Found: C,55.8; H,7.65;N,11.7; Cl,13.7;

$C_{16}H_{21}N_3O.1.35HCl.1.3H_2O$ requires C,55.8; H,7.3; N,12.2; Cl,14.0%

Water Analysis contains 2.71% $H_2O$ w/w

The following example illustrates a pharmaceutical formulation according to the invention. The active ingredient is an indole of general formula (I) or a physiologically acceptable salt or solvate thereof.

| Tablets for oral administration | |
| --- | --- |
| | mg/tablet |
| Active ingredient | 100 |
| Magnesium Stearate | 1.00 |
| Anhydrous lactose | 99 |

The active ingredient is sieved and blended with the anhydrous lactose and magnesium stearate. The mix is then compressed into tablets using a Manesty F3 tablet machine fitted with 8.0 mm concave punches.

We claim:
1. A copound of general formula (I):

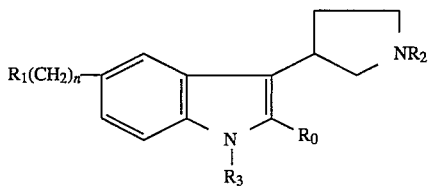

wherein $R_0$ represents a hydrogen atom or a $C_{1-3}$ alkyl group;

$R_1$ represents a group $R_4CONH-$, $R_4R_5NSO_2-$, $R_4SO_2NH-$ or $R_{14}R_5NCO-$ (where $R_4$ represents a hydrogen atom or a $C_{1-6}$ alkyl group, provided that $R_4$ does not represent a hydrogen atom when $R_1$ represents $R_4SO_2NH-$, and $R_5$ represents a hydrogen atom or a $C_{1-6}$ alkyl, $C_{3-7}$ cycloalkyl, phenyl or phen($C_{1-3}$) alkyl group in which the phenyl ring is optionally substituted by a halogen atome or a $C_{1-4}$ alkoxy, hydroxy or $C_{1-3}$ alkyl group); $R_2$ represents a hydrogen atom or a $C_{1-3}$ alkyl, $C_{3-6}$ akenyl, phenyl or phen($C_{1-3}$) alkyl group; $R_3$ represents a hydrogen atom, a $C_{1-3}$ alkyl group or a group $-CO_2R_6$, $-COR_6$, $-COCO_2R_6$ or $-CONHR_6$ where $R_6$ represents a hydrogen atom or a $C_{1-4}$ alkyl, $C_{3-7}$ cycloalkyl, $C_{3-6}$ alkenyl, aryl or ar($C_{1-4}$)alkyl group in which the aryl group may be unsubstituted or substituted by a halogen atom or a $C_{1-4}$ alkoxy, $C_{1-4}$ alkyl or hydroxy group (provided that when $R_3$ represents $-CO_2R_6$, $R_6$ is other than hydrogen);

n represents zero or an integer from 1 to 5;
or a pharmaceutically acceptable salt thereof.

2. A compound as claimed in claim 1 in which $R_1$ represents a group $R_4CONH-$.

3. A compound as claimed in claim 1 in which $R_1$ represents a group $R_4R_5NSO_2-$.

4. A compound as claimed in claim 1 in which $R_1$ represents a group $R_4SO_2NH-$.

5. A compound as claimed in claim 1 in which $R_1$ represents a group $R_4R_5NCO-$.

6. A compound as claimed in claim 1 in which $R_2$ represents a $C_{1-3}$ alkyl group or a hydrogen atom.

7. A compound as claimed in claim 1 in which $R_3$ represents a hydrogen atom.

8. A compound as claimed in claim 1 in which $R_4$ represents a hydrogen atom or a $C_{1-3}$ alkyl group.

9. A compound as claimed in claim 1 in which $R_5$ represents a $C_{1-3}$ alkyl group or a hydrogen atom.

10. A compound as claimed in claim 1 in which n represents zero or an integer from 1 to 3.

11. A compound of general formula (Ia)

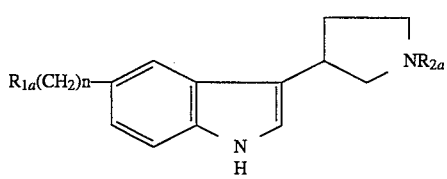

wherein $R_1a$ represents a group $R_{3a}R_{4a}NSO_2-$ where $R_{3a}$ and $R_{4a}$ are the same or different and are hydrogen or a $C_{1-6}$ alkyl group;

$R_{2a}$ represents a $C_{1-3}$ alkyl group or a hydrogen atom;

n is an integer 1 or 2;

or a pharmaceutically acceptable salt thereof.

12. A compound which is
N-methyl-3-(1-methyl-3-pyrrolidinyl)-1H-indole-5-ethanesulphonamide;
N-Methyl-3-(1-methyl-3-pyrrolidinyl)-1H-indole-5-methanesulphonamide;
or a pharmaceutically acceptable salt thereof.

13. A pharmaceutical composition which comprises a compound of formula (I) as claimed in claim 1 or a pharmaceutically acceptable salt or solvate thereof together with one or more pharmaceutically acceptable carriers or excipients.

14. A pharmaceutical composition which comprises a compound of formula (Ia) as claimed in claim 11 or a pharmaceutically acceptable salt thereof, together with one or more pharmaceutically acceptable carriers or excipients.

15. A pharmaceutical composition which comprises a compound as claimed in claim 12 or a pharmaceutically acceptable salt thereof, together with one or more pharmaceutically acceptable carriers or excipients.

16. A method of treatment of a mammal which comprises administering to a mammal suffering from a condition associated with cephalic pain an effective amount to alleviate said condition of a compound of formula (I) as claimed in claim 1 or a pharmaceutically acceptable salt thereof.

17. A method of treatment of a mammal which comprises administering to a mammal suffering from a condition associated with cephalic pain an effective amount to alleviate said condition of a compound of formula (Ia) as claimed in claim 11 or a pharmaceutically acceptable salt thereof.

18. A method of treatment of a mammal which comprises administering to a mammal suffering from a condition associated with cephalic pain an effective amount to alleviate said condition of a compound as claimed in claim 12 or a pharmaceutically acceptable salt thereof.

19. A method as claimed in claim 16 wherein the condition associated cephalic pain is cluster headache, chronic paroxysmal hemicrania, headache associated with vascular disorders, headache associated with substances or withdrawal from said substances, tension headache, or migraine.

20. A method as claimed in claim 17 wherein the condition associated with cephalic pain is cluster headache, chronic paroxysmal henicrania, headache associated with vascular disorder, headache associated with substances or withdrawal from said substances, tension headache, or migraine.

21. A method as claimed in claim 18 wherein the condition associated with cephalic pain is cluster headache, chronic paroxysmal hemicrania, headache associated with vascular disorders, headache associated with substances or withdrawal from said substances, tension headache, or migraine.

* * * * *